(12) United States Patent
Nickel et al.

(10) Patent No.: US 6,696,428 B2
(45) Date of Patent: Feb. 24, 2004

(54) USE OF DOPAMINE RECEPTOR ANTAGONISTS IN PALLIATIVE TUMOR THERAPY

(75) Inventors: Bernd Nickel, Mühital (DE); Peter Hilgard, Frankfurt (DE); Thomas Klenner, Ingelheim (DE); Jürgen Engel, Alzenau (DE)

(73) Assignee: Zentaris AG, Frankfurt/Main (DE)

( * ) Notice: Subject to any disclaimer, the term of this patent is extended or adjusted under 35 U.S.C. 154(b) by 0 days.

(21) Appl. No.: 10/210,881

(22) Filed: Aug. 2, 2002

(65) Prior Publication Data

US 2003/0008846 A1 Jan. 9, 2003

Related U.S. Application Data

(62) Division of application No. 09/599,561, filed on Jun. 23, 2000, now Pat. No. 6,576,624, which is a continuation of application No. 08/986,235, filed on Dec. 5, 1997, now Pat. No. 6,093,704.

(30) Foreign Application Priority Data

Dec. 6, 1996 (DE) ......................... 196 50 778

(51) Int. Cl.$^7$ ..................... A61K 31/685; A61K 31/445
(52) U.S. Cl. ......................... 514/77; 514/322
(58) Field of Search ................... 514/77, 322

(56) References Cited

U.S. PATENT DOCUMENTS

| 4,707,484 A | 11/1987 | Berger et al. |
| 4,883,822 A | 11/1989 | Matsuo et al. |

FOREIGN PATENT DOCUMENTS

| EP | 0 273 168 | 7/1988 |

OTHER PUBLICATIONS

Willis et al., Pharmacol Biochem Behav, (1988) 31 (1), 69–74 Abstract Only.*
Hilgard et al., Advances in Experimental Medicine and Biology (1996) 416, 157–164 Abstract Only.*
"A dose–finding study of miltefosine (hexadecylphosphocholine) in patients with metastatic solid tumors"; Verweij, J. Planting, A., van der Burg M., Stofer, G.; Department of Medical Oncology, Rotterdam Cancer Institute/Daniel den Hoed Kliniek, The Netherlands; J Cancer Res Clin Oncol 1992; 118(8):606–8.
"Phase II study of daily oral miltefosine (hexadecylphosphocholine) in advanced colorectal cancer"; Planting AS, Stoter, G., Verweij, J.; Department of Medical Oncology, Rotterdam Cancer Institute/Dr. Daniel den Hoed Kliniek, The Netherlands; Eur J Cancer 1993; 29A(4):518–9.
Rote Liste 1998; Arzneimittelverzeichnis des Bundesverbandes der Pharmazeutischen Industre e. V. (BPI), des Verbandes Forschender Arzeimittelhersteller e. V. (VFA), des Bundesfachverbandes der Arzneimittel–Hersteller e. V. (BAH) und des Verbnades aktiver Pharmaunternehmen e.V. (VAP); ECV, Editio Cantor, Aulendorf/Wurtt.
"Effects of domperidone in patients with chronic unexplained upper gastrointestinal symptoms: a double–blind, placebo–controlled study"; Davis RH. Clench MH, Mathias JR; Department of Medicine, College of Medicine, University of Florida, Gainesville, Dig Dis Sci 1988 Dec; 33(12): 1505–11.
Nickel et al.: "D–21266: A New Antitumor Alkylphosphocholine Derivative with Less Side Effects", Proc. Annu. Meet. Am. Assoc. Cancer Res., Bd. 38, 1997, p. A4102.
Verweij et al., "Phase II Study of Oral Miltefosine in Patients with Squamous Cell Head and Neck Cancer", Eur. J. Cancer, vol. 29A., No. 5, 1993, pp. 778–779.
Willis et al., Pharmacol., Biochem. Behav., 31(1), 69–73.
Frussa–Filho et al., Braz. J. Med. Biol. Res., 24(6), 611–14.
.Spruse et al., J. Cancer Res. Clin. Oncol., 119(3), 142–9.

* cited by examiner

*Primary Examiner*—Jerome D. Goldberg
(74) *Attorney, Agent, or Firm*—Pillsbury Winthrop LLP

(57) ABSTRACT

The side effect of decrease in body weight caused by the alkylphosphocholines such as miltefosine can be antagonized by certain acetylcholine receptor antagonists such as domperidone and pimozide. The combination of alkylphosphocholine plus the antagonist does not have any effect on the anti-tumor action of the alkylphosphocholine. The combination also caused no new side effects in the animals.

9 Claims, 12 Drawing Sheets

USE OF DOPAMINE RECEPTOR ANTAGONISTS IN PALLIATIVE TUMOR THERAPY

CROSS-REFERENCE TO RELATED APPLICATION

This is a divisional of Ser. No. 09/599,561 filed Jun. 23, 2000 now U.S. Pat. No. 6,576,624 which is a continuation of 08/986,235 filed Dec. 5, 1997 now U.S. Pat. No. 6,093,704 which claims priority to German Application No. 19650778.2 filed Dec. 6, 1996.

BACKGROUND OF THE INVENTION

1. Field of the Invention

The invention relates to the use of dopamine receptor antagonists in palliative tumor therapy, particularly as agents for antagonizing side effects such as are frequently observed in tumor therapy by means of alkylphosphocholines, particularly miltefosine.

2. Background Information

It is known and described that the alkylphosphocholine miltefosine causes side effects in patients during the treatment of cancer. These also manifest themselves in patients treated with miltefosine by a marked loss of body weight (*Eur. J. Cancer*, Vol. 29 A, No. 2, pp. 208–209, 1993). Further side effects of the chemotherapy are: damage to the tissue with a high proliferation rate, leuko- and thrombopenia, decrease in erythrocytes, gastrointestinal disorders, loss of appetite, upper abdominal complaints, disturbed absorption and diarrhea, as well as loss of hair and also liver damage and hyperuricaemia.

In a dose-finding study by J. Verweij et al. (*J. Cancer Res. Clin. Oncol* 118:606–608 (1992)), it was observed that most antiemetics (including $5HT_3$ antagonists) were inactive in the prevention of vomiting and nausea. The smallest emetic effect was achieved if miltefosine was taken immediately after eating, domperidone being given 0.5 hours before eating in a dose of 20 mg. In the phase II studies of the same author which were carried out later (*Eur. J. Cancer* Vol. 29 A, No. 5 p. 779(1993)), it was meanwhile found that it was not possible to prevent vomiting either by standard antiemetics or by $5HT_3$ antagonists.

Since the loss of weight under tumor treatment with alkylphosphocholines leads to a further weakening of the already overloaded body, it was the object of the invention to characterize substances which, in combination with miltefosine or its derivatives, antagonize the known side effects of the alkylphosphocholines such as decrease in body weight.

It must be ensured here that the anti-tumor action of miltefosine or its derivatives is not abolished or reduced by combination with the antidote and no additional side effects occur due to the administration of the combination.

SUMMARY OF THE INVENTION

The above object has now been achieved in that agents for antagonizing side effects such as are frequently observed during tumor therapy by means of alkylphosphocholines, in particular miltefosine, have been found and prepared. These are dopamine receptor antagonists, particularly the two dopamine antagonists domperidone and pimozide. It is to be understood that these agents can be administered both in a fixed combination with the alkylphosphocholine and, in each case, in individual packs and sequentially.

DETAILED DESCRIPTION OF THE INVENTION

EXAMPLE

Experimental Results

Figure 1:
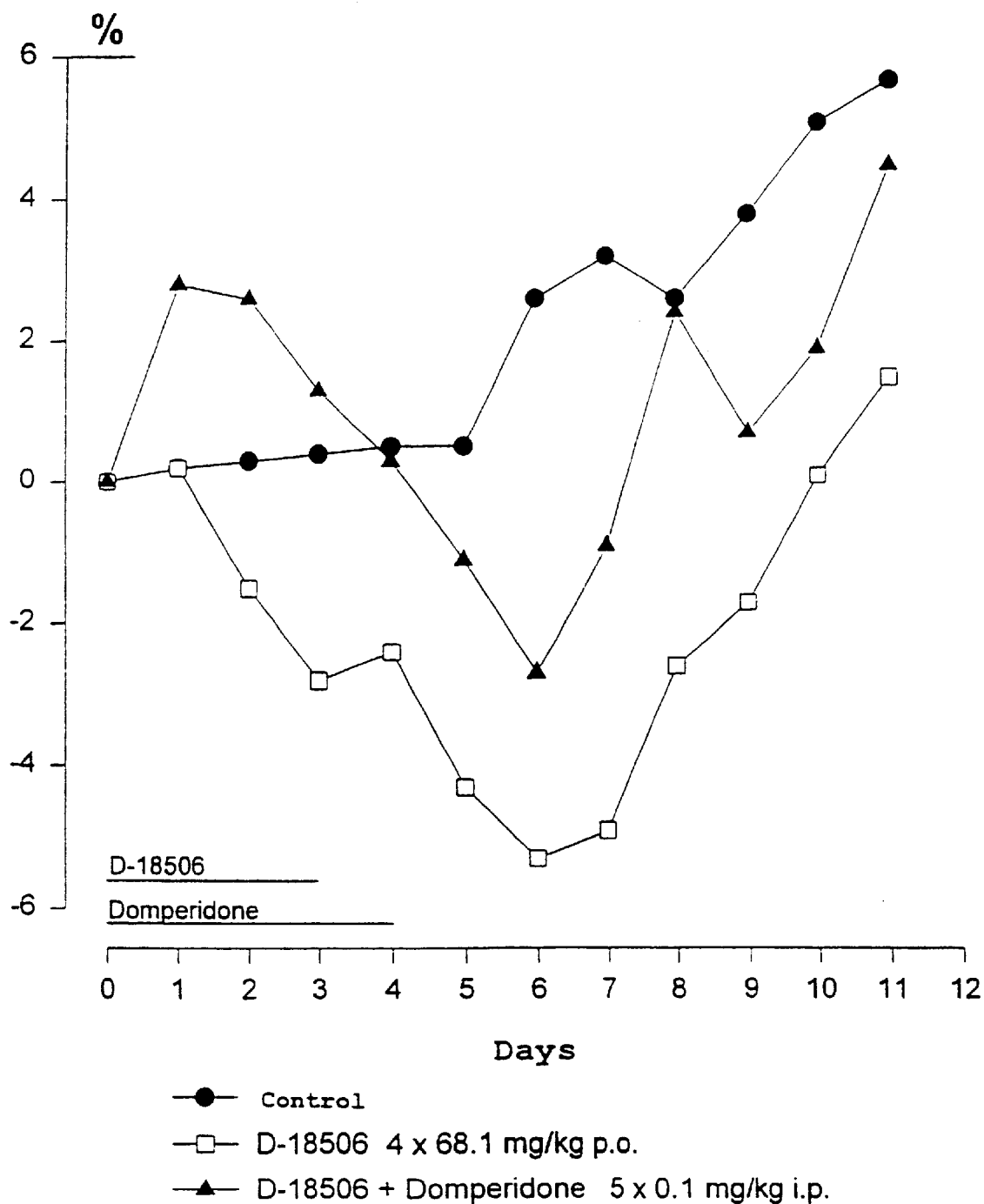
FIG. 1 shows effects of D-18506 (miltefosine) and domperidone on the body weight of normal rats.
Figure 2:
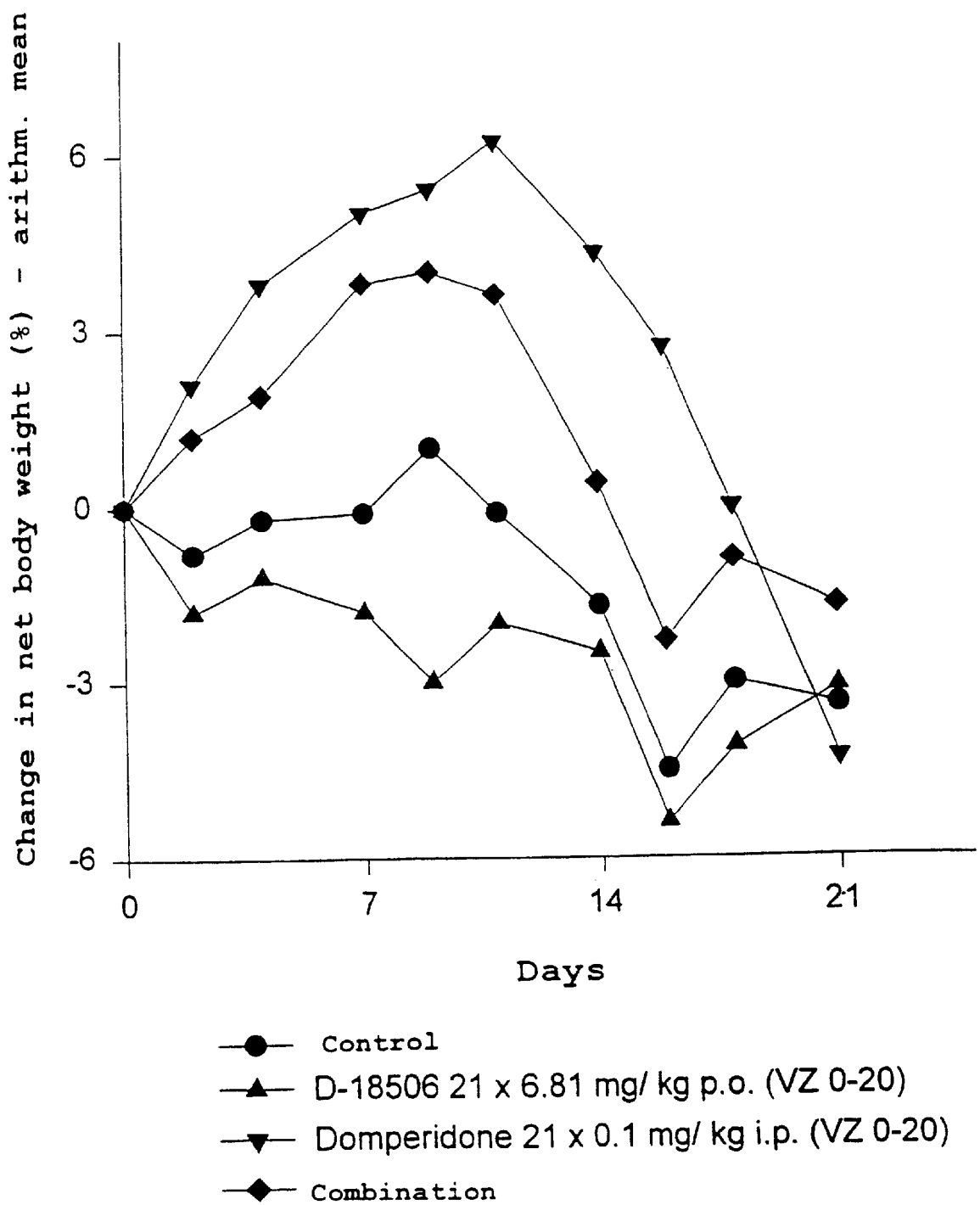
FIG. 2 shows effects of D-18506 (miltefosine) and domperidone on the body weight of rats with DMBA-induced breast tumor.
Figure 3:
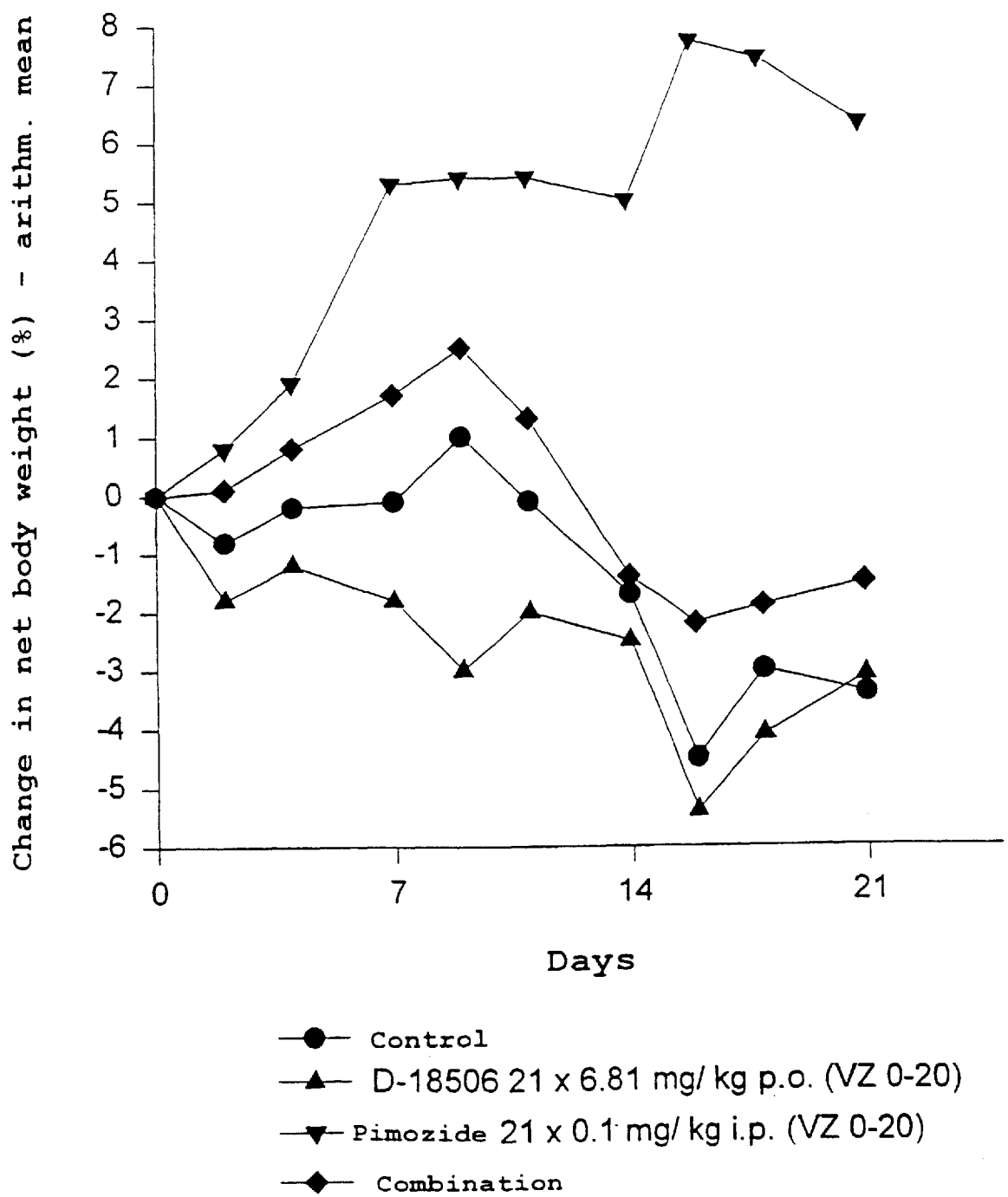
FIG. 3 shows effects of D-18506 (miltefosine) and pimozide on the body weight of rats with DMBA-induced breast tumor.
Figure 4:
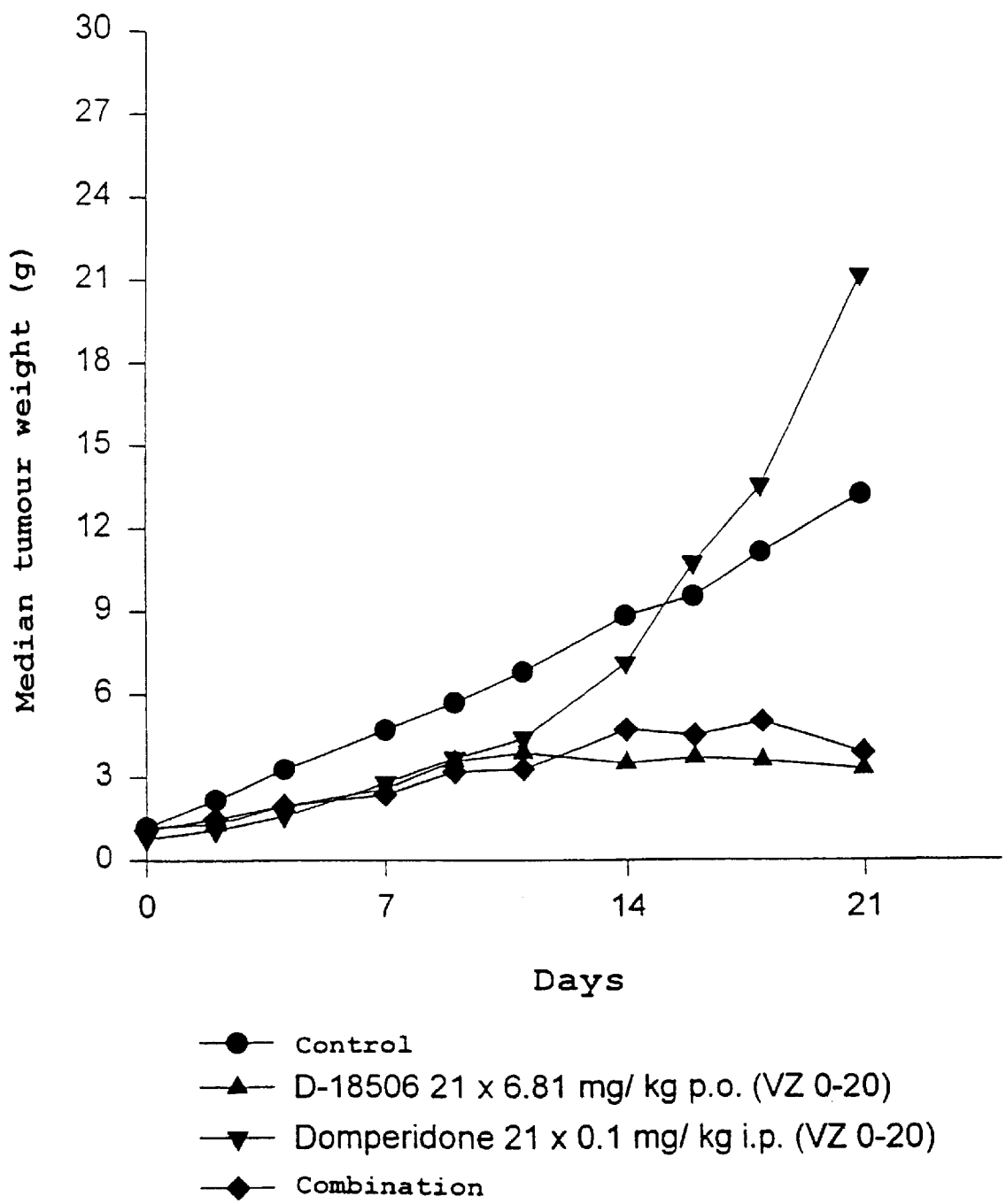
FIG. 4 shows effects of D-18506 (miltefosine) and domperidone on DMBA-induced breast tumor of rats.
Figure 5:
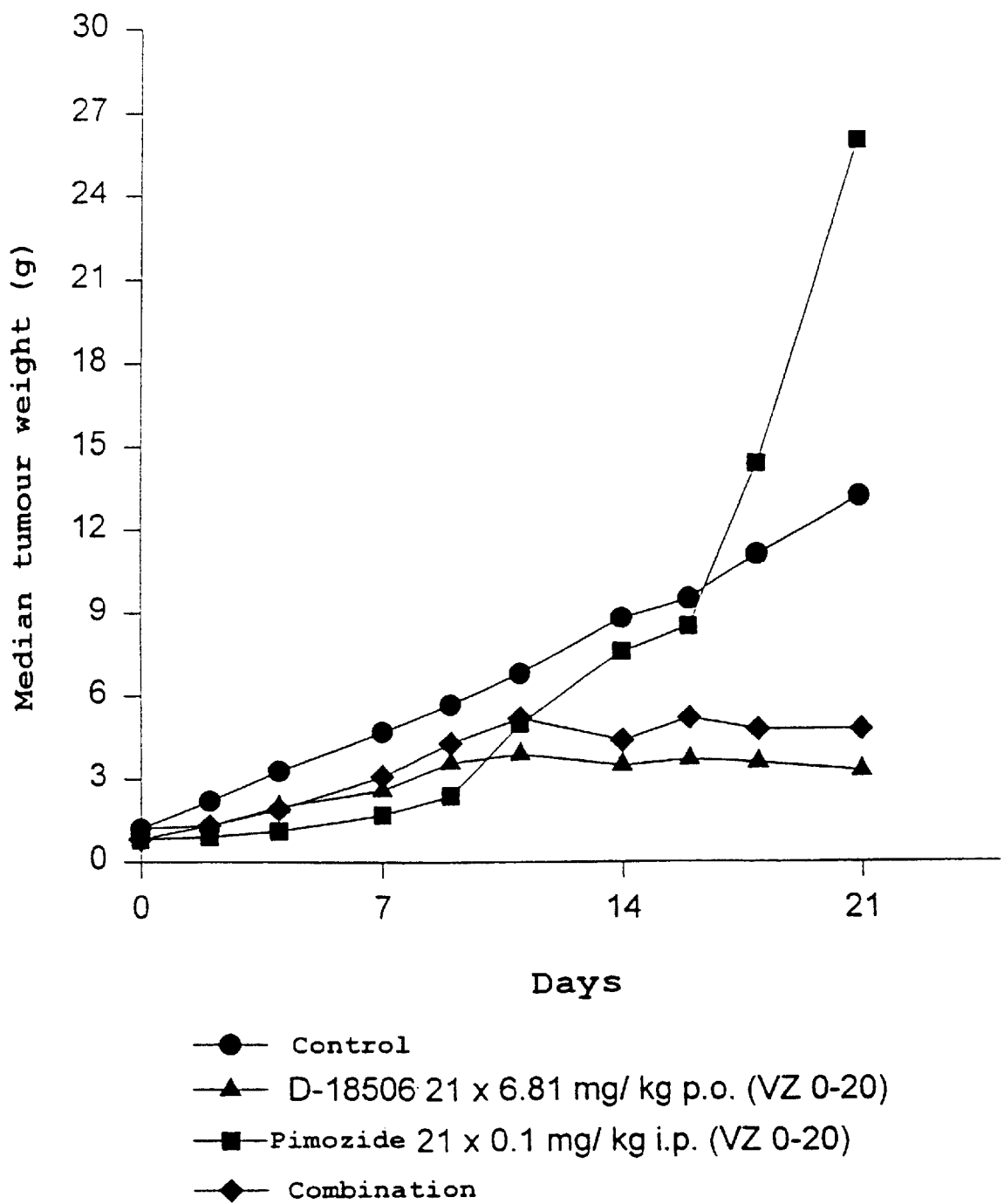
FIG. 5 shows effects of D-18506 (miltefosine) and pimozide on DMBA-induced breast tumor of rats.

Comparative studies with respect to body weight changes in healthy and tumor-bearing rats were investigated after administration of miltefosine or octadecyl (1,1-dimethylpiperidinio-4-yl) phosphate alone and in combination with various appetite-stimulating compounds. On administration of miltefosine alone, there is a clear loss of weight in the two groups of animals. This is significantly antagonized by the simultaneous administration of domperidone (5×0.1 mg/kg i.p.) or pimozide (5×0.1 mg/kg i.p.) (dopamine antagonists). These effects are observed both in healthy and in tumor-bearing animals (FIGS. 1–3; Table 1). The anti-tumor action of miltefosine is not affected in combination with the two antidotes (FIGS. 4 and 5).

TABLE 1

| Changes of body weight (rat) | | | | |
|---|---|---|---|---|
| | Control AUC | | D-18506 (4 × 68.1 mg/kg p.o.) AUC | |
| day | 7 | 11 | 7 | 11 |
| mg/kg i.p. | 6.2 | 22.4 | −17.9 | −23.5 |
| Domperidone 0.1 | 28.6** | 62.8** | 28.6** | 62.8 |
| Domp. + D-18506 | 2.7 | 10.2 | 2.7** | 10.2* |
| Pimozide 0.2 | 30.4** | 69.8** | 30.4** | 69.8** |
| Pimo. + D-18506 | 4.6 | 12.4 | 4.6 | 12.4 |
| Metoclopramide 0.2 | 11.5 | 30.5 | 11.5** | 30.5** |

TABLE 1-continued

Changes of body weight (rat)

| | Control AUC | | D-18506 (4 × 68.1 mg/kg p.o.) AUC | |
|---|---|---|---|---|
| day | 7 | 11 | 7 | 11 |
| mg/kg i.p. | 6.2 | 22.4 | −17.9 | −23.5 |
| Meto. + D-16506 | −21.4 | −36.6 | −21.4 | −36.6 |
| Cyproheptadine 2.5 | 0.8 | 15.5 | 0.8 | 15.5 |
| Cypro. + D-18506 | −30.1 | 57.6 | −30.1 | −57.6 |

ACU = Area under the curve
Dunnett's T test for variable (AUC)
**$p < 0.05$ in comparison with the control group
*$p < 0.10$ The decrease in weight in the healthy and tumor-bearing animals which received miltefosine in combination with the dopamine receptor antagonists domperidone or pimozide turns out to be significantly lower than in the rats only treated with miltefosine. The control value (placebo-treated animals), however, is not reached.

Figure 6:
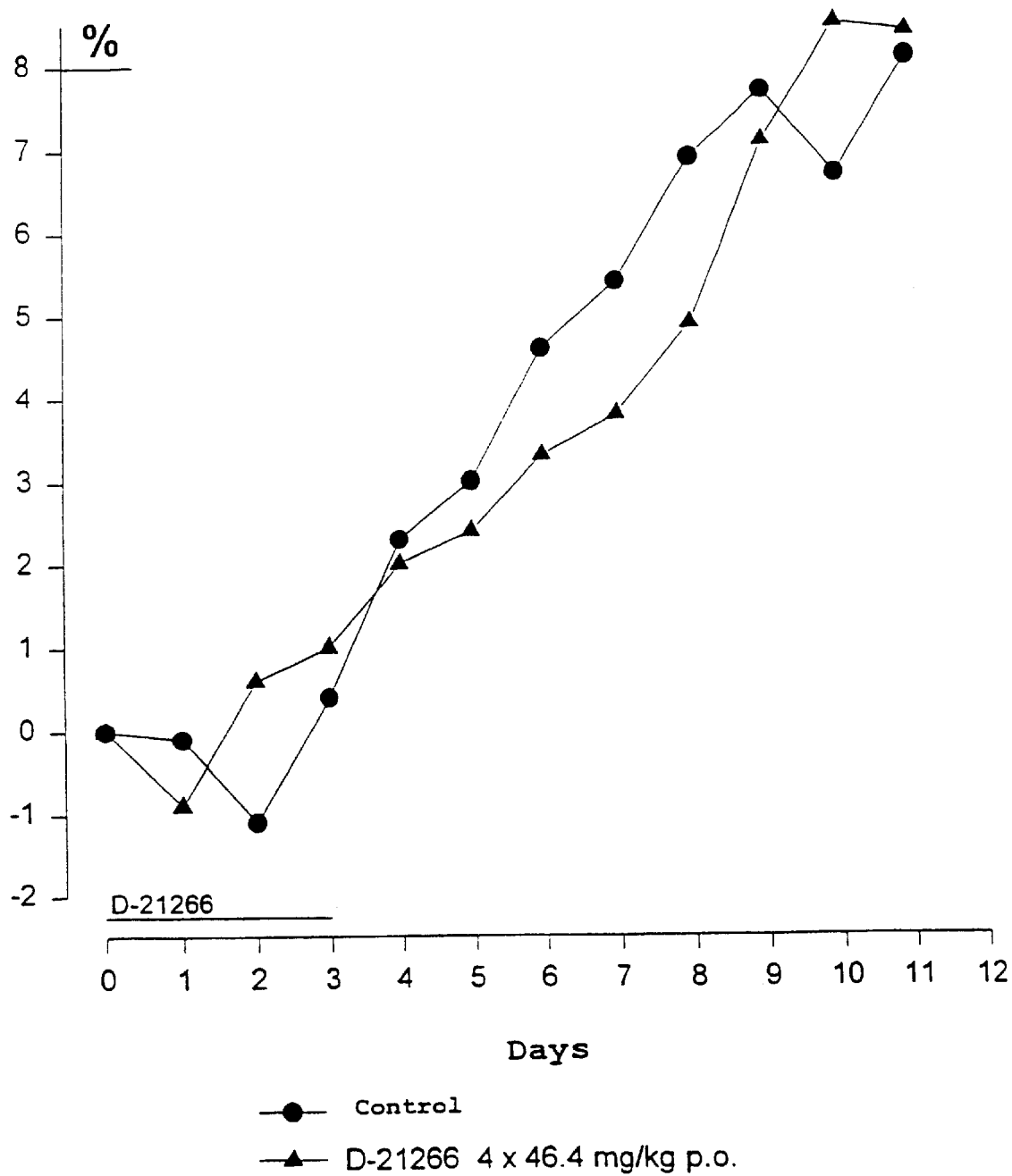
FIG. 6 shows effects of D-21266 (octadecyl (1,1-dimethylpiperidinio-4-yl)phosphate) on the body weight of normal rats.
Figure 7:
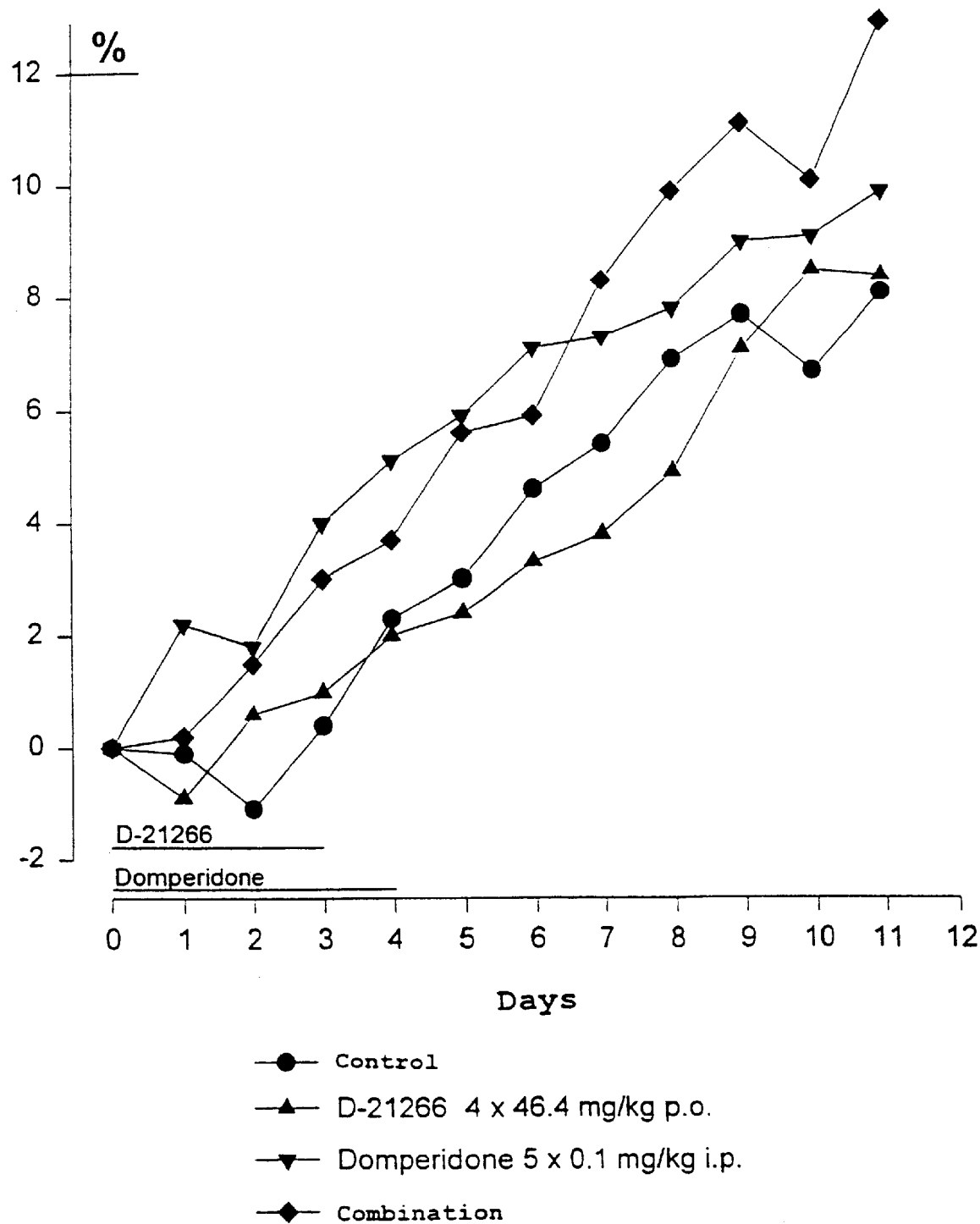
FIG. 7 shows effects of D-21266 (octadecyl (1,1-dimethylpiperidinio-4-yl)phosphate) and domperidone on the body weight of normal rats.
Figure 8:
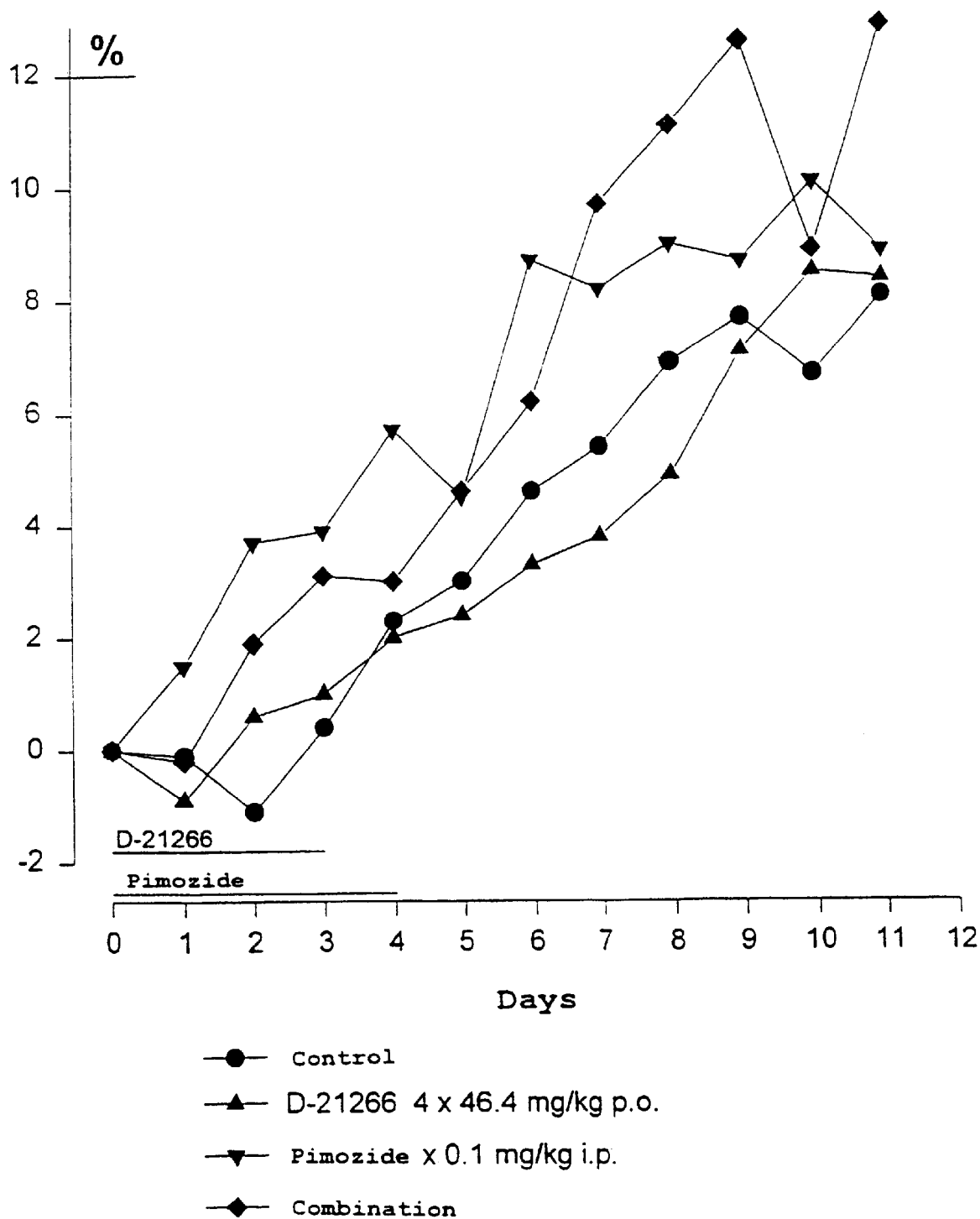
FIG. 8 shows effects of D-21266 (octadecyl (1,1-dimethylpiperidinio-4-yl)phosphate) and pimozide on the body weight of normal rats.
Figure 9:
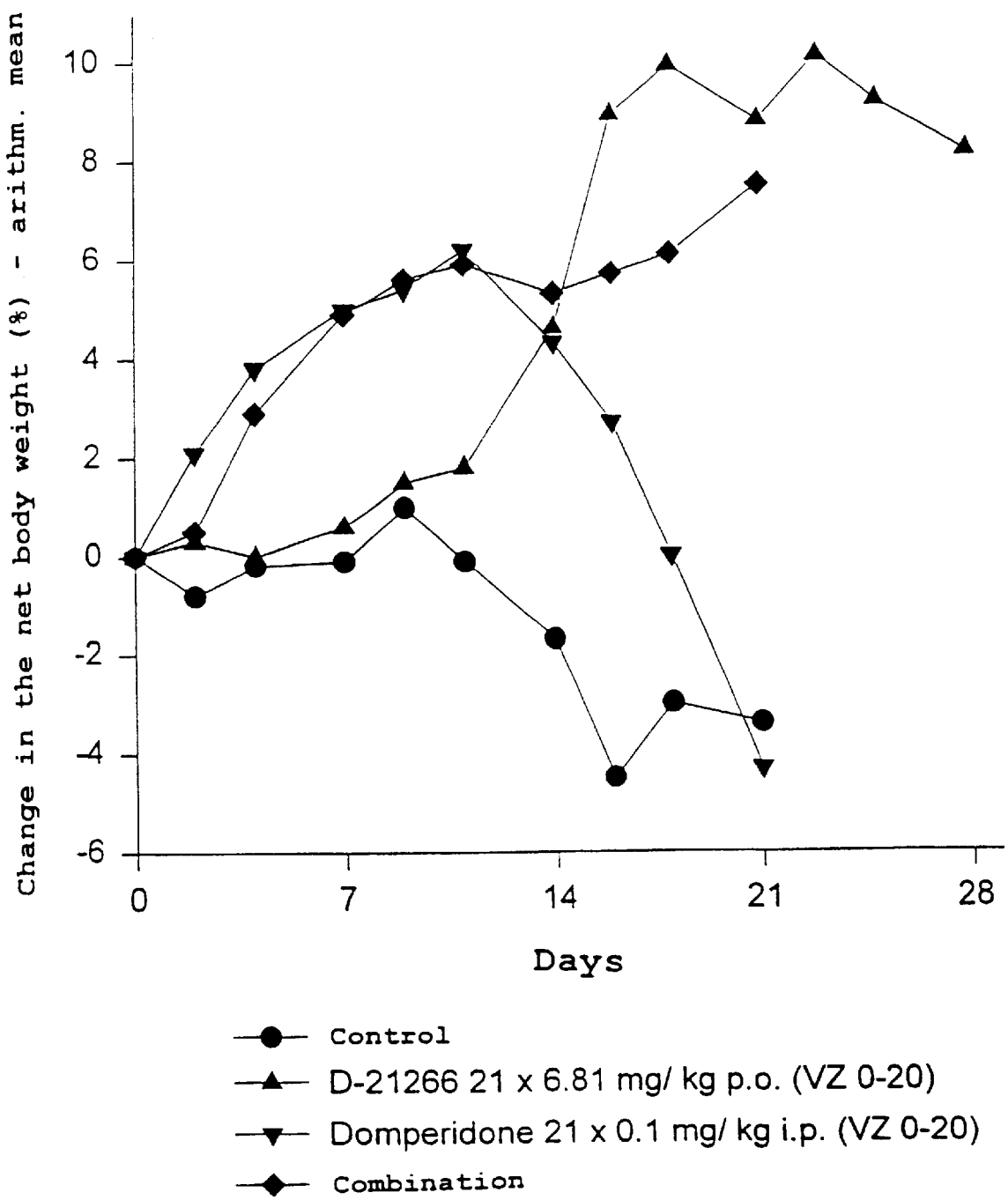
FIG. 9 shows effects of D-21266 (octadecyl (1,1-dimethylpiperidinio-4-yl)phosphate) and domperidone on the body weight of rats with DMBA-induced breast tumor.
Figure 10:
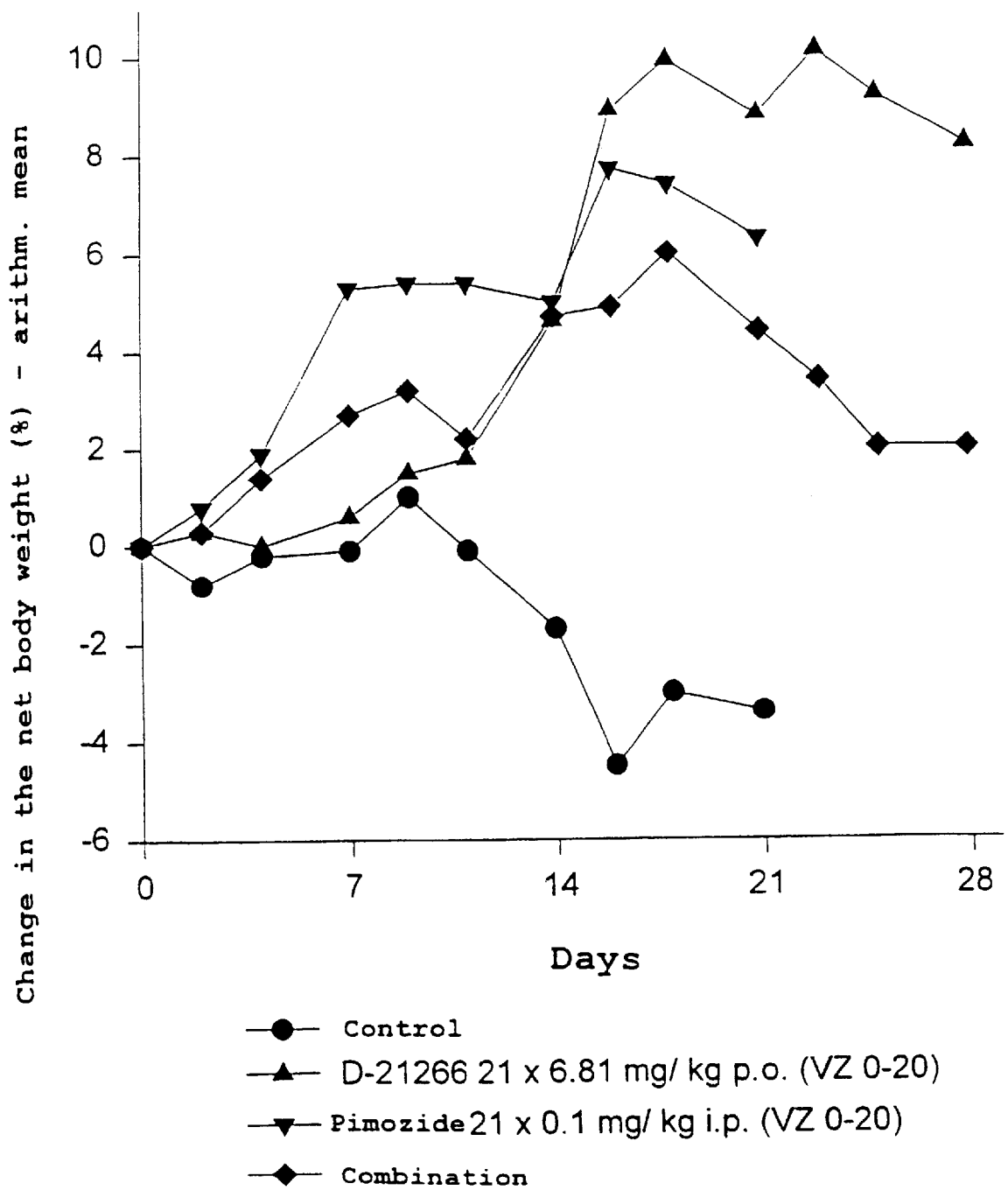
FIG. 10 shows effects of D-21266 (octadecyl (1,1-dimethylpiperidinio-4-yl)phosphate) and pimozide on the body weight of rats with DMBA-induced breast tumor.
Figure 11:
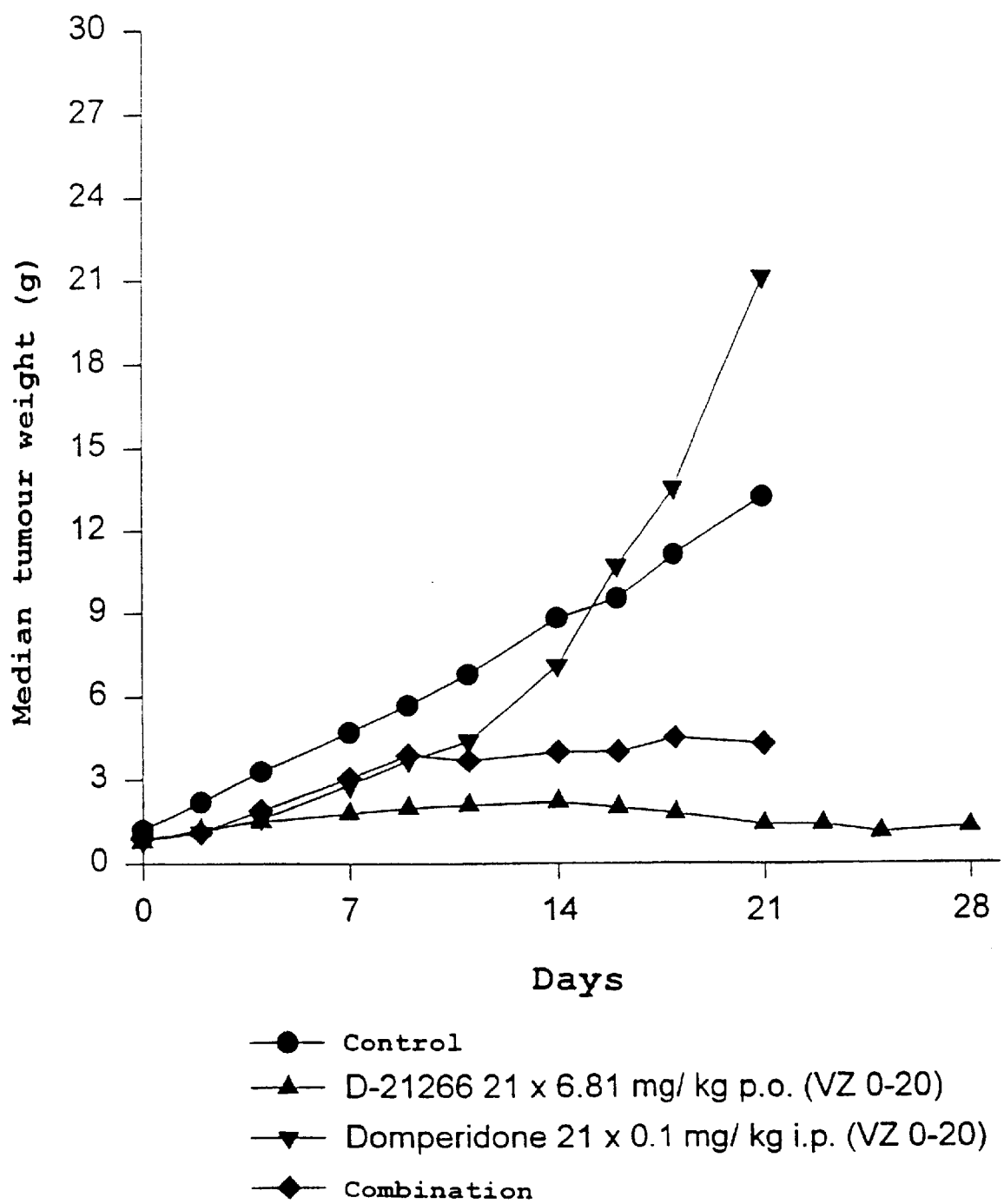
FIG. 11 shows effects of D-21266 (octadecyl (1,1-dimethylpiperidinio-4-yl)phosphate) and domperidone on DMBA-induced breast tumor in rats.
Figure 12:
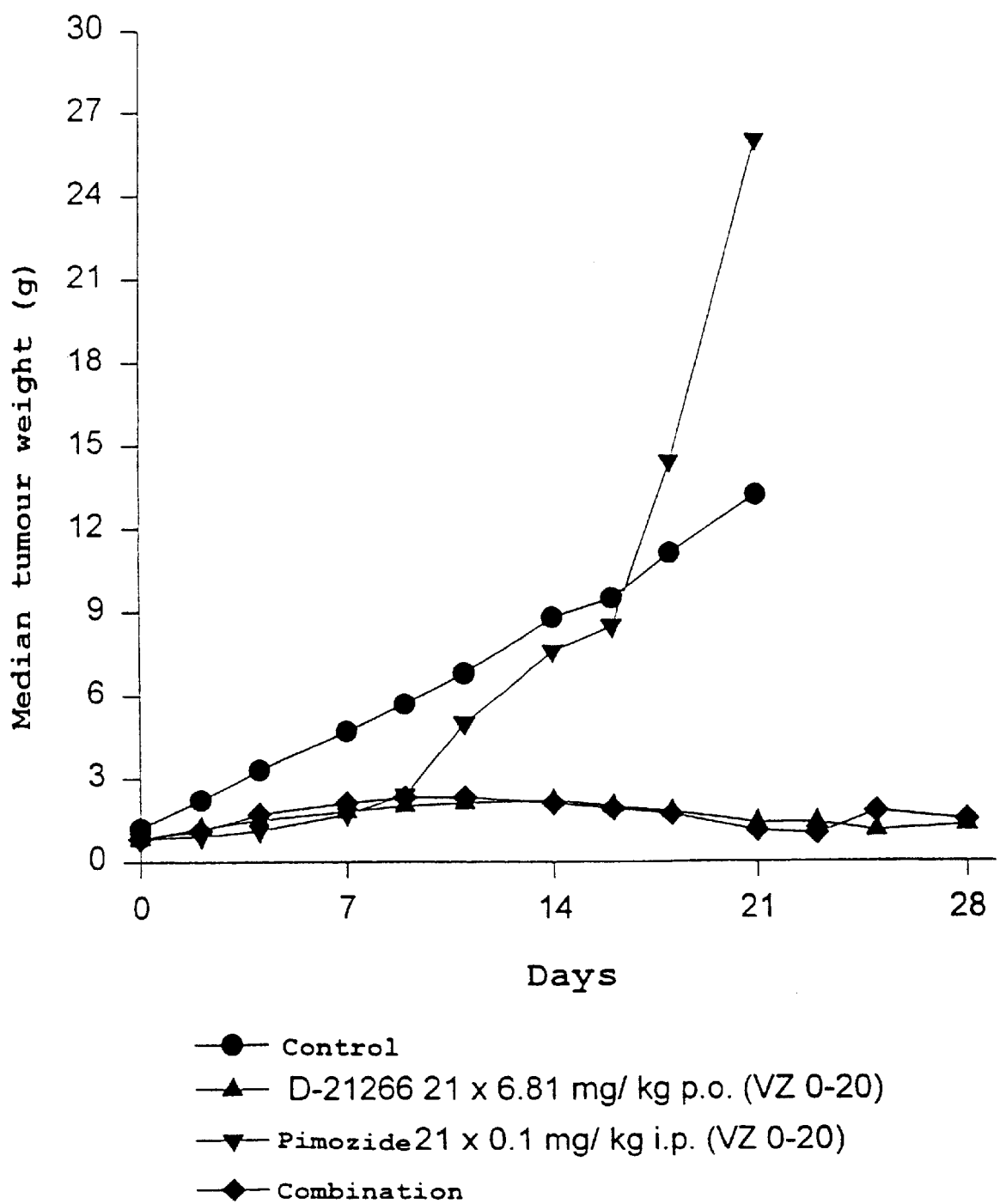
FIG. 12 shows effects of D-21266 (octadecyl (1,1-dimethylpiperidinio-4-yl)phosphate) and pimozide on DMBA-induced breast tumor in rats.

After administration of the alkylphosphocholine derivative octadecyl (1,1-dimethylpiperidinio-4-yl)-phosphate, there is a lower loss of weight in the with miltefosine. The rats increase in weight less than the control animals (FIG. 6). By the simultaneous administration of the dopamine receptor antagonists domperidone or pimozide, the slower increase in weight of the animals treated with octadecyl (1,1-dimethylpiperidinio-4-yl)phosphate is more than compensated. The animals are actually markedly heavier than the control animals only treated with placebo (FIGS. 7 and 8).

The two other appetite-stimulating compounds cyproheptadine and metoclopramide (serotonin receptor antagonists) in combination with octadecyl (1,1-dimethylpiperidinio-4-yl)phosphate had no significant effect on the body weight development of the animals (Table 2).

TABLE 2

Changes of body weight (rat)

| | Control AUC | | D-21266 (4 × 46.4 mg/kg p.o.) AUC | |
|---|---|---|---|---|
| day | 7 | 11 | 7 | 11 |
| mg/kg i.p. | 11.8 | 39.8 | 10.6 | 37.1 |
| Pimozide 0.1 | 31.2** | 67.5** | 31.2** | 67.5** |
| Pimo. + D-21266 | 23.5 | 67.3** | 23.5* | 67.3** |
| Cyproheptadine 2.5 | 1.5 | 20.6 | 1.5 | 20.6 |
| Cypro. + D-21266 | −18.1 | −41.2 | 18.1 | −41.2 |
| Metoclopramide 0.2 | 19.2 | 49.4 | 19.2 | 49.4 |
| Meto. + D-21266 | 18.4 | 46.6 | 18.4 | 46.6 |
| Domperidone 0.1 | 28.6** | 62.8** | 28.6** | 62.8** |
| Domp. + D-21266 | 27.9** | 66.1** | 27.9** | 66.1** |

ACU = Area under the curve
Dunnett's T test for variable (AUC)
**$p < 0.05$ in comparison with the control group
*$p < 0.10$ In Tumor-bearing animals, the same picture results as in healthy animals. Domperidone and pimozide alone and in combination with octadecyl (1,1-dimethylpiperidinio-4-yl) phosphate increase the body weight development of the animals without affecting the anti-tumor action (FIGS. 9–12).

The doses of the antidote were selected such that the compounds themselves caused no side effects at all in the experimental animals.

These results are surprising since the combination of miltefosine with the similarly appetite-stimulating substances metoclopramide or cyproheptadine does not lead to any positive effect on the decrease in weight in the animals. In contrast, there is instead an increase in the loss of weight (Table 1). A therapeutic use of dopamine receptor antagonists such as pimozide or domperidone was also in no way suggested by the contradictory statements in the art with respect to the effect on nemesis and nausea.

What is claimed is:

1. A composition comprising:
   an amount of octadecyl (1,1-dimethylpiperidinio-4-yl) phosphate therapeutically effective for treatment of a cancer sensitive to octadecyl (1,1-dimethylpiperidinio-4-yl)phosphate, and
   an appetite-stimulating dopamine receptor antagonist present in an amount effective to reduce a side effect of said octadecyl (1,1-dimethylpiperidinio-4-yl) phosphate and a pharmaceutically acceptable carrier, wherein the amount of appetite-stimulating dopamine receptor antagonist used is not effective for the treatment of said cancer sensitive to octadecyl (1,1-dimethylpiperidinio-4-yl)phosphate.

2. A dose unit of the composition of claim 1, comprising up to about 300 mg of octadecyl (1,1-dimethylpiperidinio-4-yl)phosphate and an appetite-stimulating dopamine receptor antagonist selected from the group consisting of about 10 to about 120 mg of domperidone and about 2 to about 16 mg of pimozide.

3. A dose unit according to claim 2 comprising about 30 mg of domperidone.

4. A dose unit according to claim 2 comprising about 4 mg of pimozide.

5. A method of treating a side effect of octadecyl (1,1-dimethylpiperidinio-4-yl)phosphate in a mammal being administered octadecyl (1,1-dimethylpiperidinio-4-yl) phosphate for a cancer sensitive to octadecyl (1,1-dimethylpiperidinio-4-yl)phosphate comprising:
   administering to said mammal an appetite-stimulating dopamine receptor antagonist in an amount effective to reduce a side effect of an amount of octadecyl (1,1-dimethylpiperidinio-4-yl)phosphate therapeutically effective for said cancer, wherein the amount of appetite-stimulating dopamine receptor antagonist used is not effective for the treatment of said cancer sensitive to octadecyl (1,1-dimethylpiperidinio-4-yl)phosphate, and
   wherein the appetite-stimulating dopamine receptor antagonist is either concurrently or sequentially administered with respect to the octadecyl (1,1-dimethylpiperidinio-4-yl)phosphate.

6. The method according to claim 5, wherein said appetite-stimulating dopamine receptor antagonist is administered simultaneously with said octadecyl (1,1-dimethylpiperidinio-4-yl)phosphate.

7. The method according to claim 6, wherein up to about 300 mg/day of octadecyl (1,1-dimethylpiperidinio-4-yl) phosphate is administered with an amount of dopamine receptor antagonist selected from the group consisting of about 10 to about 120 mg/day of domperidone and about 2 to about 16 mg/day of pimozide.

8. The method according to claim 7, wherein about 30 mg/day of domperidone is administered.

9. The method according to claim 7, wherein about 4 mg/day of pimozide is administered.

* * * * *